United States Patent
Lanér

(10) Patent No.: US 6,510,196 B2
(45) Date of Patent: Jan. 21, 2003

(54) DETERMINATION AND ADJUSTMENT OF EXPOSURE VALUES FOR X-RAY IMAGING

(75) Inventor: Kai Valter Lanér, Helsinki (FI)

(73) Assignee: Instrumentarium Corporation (FI)

( * ) Notice: Subject to any disclaimer, the term of this patent is extended or adjusted under 35 U.S.C. 154(b) by 18 days.

(21) Appl. No.: 09/872,158

(22) Filed: Jun. 4, 2001

(65) Prior Publication Data

US 2002/0034277 A1 Mar. 21, 2002

(30) Foreign Application Priority Data

Jun. 2, 2000 (EP) .............................. 00660104

(51) Int. Cl.[7] .................................. A61B 6/14
(52) U.S. Cl. .................... 378/39; 378/110; 378/112; 378/168
(58) Field of Search .............. 378/38, 39, 40, 378/108, 109, 110, 111, 112, 168, 193, 195, 197

(56) References Cited

U.S. PATENT DOCUMENTS

| | | | |
|---|---|---|---|
| 4,242,585 A | 12/1980 | Yamano | 378/39 |
| 4,439,867 A | 3/1984 | Yoshida | 378/96 |
| 4,597,094 A | 6/1986 | Kleinman | 378/95 |
| 4,641,331 A * | 2/1987 | Makino et al. | 378/108 |
| 4,694,478 A * | 9/1987 | Delnon | 378/39 |
| 4,783,793 A | 11/1988 | Virta et al. | 378/39 |
| 5,386,448 A | 1/1995 | Tammisalo et al. | 378/38 |
| 5,828,720 A | 10/1998 | Syrjänen | 378/38 |
| 6,018,563 A * | 1/2000 | Arai et al. | 378/39 |

FOREIGN PATENT DOCUMENTS

| | | |
|---|---|---|
| DE | 30 35 435 | 4/1981 |
| EP | 229 972 B1 | 12/1986 |

* cited by examiner

Primary Examiner—Drew A. Dunn
Assistant Examiner—Therese Barber
(74) Attorney, Agent, or Firm—Banner & Witcoff, Ltd.

(57) ABSTRACT

A device for determining exposure values in an X-ray panoramic and/or cephalometric apparatus (20) for imaging patient's head (3). The apparatus comprises adjustable support means (11) provided with support elements (1a, 1b) with a variable spacing (W1) therebetween, and said support means being adapted for positioning against the patient's head prior to exposure. A sensor (2) is connected to said support elements and it provides an electrical output proportional to the dimension (W2) of the patient's head therebetween. An exposure control means (10) adjust the tube current and/or the tube voltage of the X-ray tube and/or the exposure time to be at one of a plurality of predetermined levels.

14 Claims, 5 Drawing Sheets

It and/or Ut and/or T

It and/or Ut and/or T

DETERMINATION AND ADJUSTMENT OF EXPOSURE VALUES FOR X-RAY IMAGING

BACKGROUND OF THE INVENTION

The invention relates to a device for determining exposure values in an X-ray panoramic and/or cephalomretric apparatus for imaging patient's head or a part thereof, which apparatus comprises an X-ray tube, an exposure control means providing a tube voltage, a tube current and an exposure time, and adjustable support means for a patient's head, said support means being provided with at least two support elements with a variable spacing therebetween on the opposite sides of the patient's head, and said support means being adapted for positioning against the patient's head prior to an exposure. The invention also relates to a method for determining exposure values for an X-ray panoramic and/or cephalometric imaging of a patient's head, in which method: an individual spacing between the opposite sides of the patient's head is detected; exposure values are defined dependent on said detected spacing; and said exposure values are used for the imaging of the patient's head or a section thereof.

When an X-ray image is exposed the tube current (mA—value) and tube voltage (kV —value) of the X-ray tube and the exposure time (seconds) of the image receptor, called in general form as exposure values, shall be in a proper level in order that the exposed image would have a good quality. The exposure values depend on e.g. the bone thickness of the individual person or patient, who is in each case the target of the imaging. The most simple method to determine the exposure values, i.e. the tube current and the tube voltage and the exposure time, is to manually evaluate the size the person/patient in question, and thereafter to adjust the exposure values accordingly, whereupon for a taller person, like adult men, a higher tube current and/or tube voltage and/or a longer exposure time is selected, for a person of a medium size, like adult women, a somewhat lower tube current and/or tube voltage and/or a shorter exposure time is selected, and for children considerably lower tube current and/or tube voltage and/or a shorter exposure time is selected. This selection according to the type of the person can be marked on a tube current and/or a tube voltage selector and/or on an exposure time selector effecting on a timer or rotational speed control unit of the panoramic/cephalometric apparatus, whereupon the exposure value selection is a very easy and rapid procedure. The accuracy of this kind of manual exposure value selection is however very low, because of the personal evaluations by individual operators, which is a serious drawback.

Accordingly many different exposure automatics have been developed, as disclosed e.g. in documents U.S. Pat. No. 5,386,448, U.S. Pat. No. 5,828,720 and EP-0 229 972 B1, which automatics have that common feature, that the radiation penetrated through some portion of the patient, either within the target area or in an area nearby the target area of the patient, is measured with a radiation detector and the detected radiation intensity is used for adjusting the exposure values. The accuracy of these methods are generally very good, because they measure the actual radiation which is to be received by the radiation sensitive film or image plate. These types of exposure automatics have complicated measuring circuits and expensive components, and further the operators shall have good competence and carefulness in use and maintenance of the apparatuses.

An alternative apparatus and method is suggested in document DE-30 35 435 A1, which describes a measuring gauge comprising a fixed scale, which has a measuring jaw in one end thereof, and a movable scale, which has another measuring jaw parallel with the jaw of the fixed scale, whereupon one of the scales is provided with a measure graduation including the values of the tube voltage and/or tube current needed for an X-ray panoramic imaging, and the other of the scales is provided with a reading element for reading the measure graduation, and whereupon the gauge has such dimensions that the jaws can be positioned against the opposite sides of a patient. This gauge is so in principle just like those gauges, which are in general use e.g. in the engineering industry, with the exception that it is graduated using voltage/current values instead of mechanical dimensions. The accuracy as such can be acceptable, but the use of the gauge is time consuming and transferring the exposure data from the gauge to the X-ray imaging apparatus can lead to human errors if not performed carefully enough.

SUMMARY OF THE INVENTION

So the first object of the invention is to minimize the possibilities to human errors and to provide an acceptable accuracy for exposure values of the X-ray tube as compared to the size of the patient in a panoramic and/or cephalometric imaging, in which the target of the image is within the area of patient's head. In this context the jaws with teeth and/or the neck area, like cervical spinea with the lower cranial section, and/or the whole head of a patient are typically the targets, from which images shall be taken. The second object of the invention is to minimize the time used for the measuring, which time should approach nil, if only possible. The third object of the invention is to enable such measuring conditions that the size difference among adults and children respectively would not effect erroneous exposure values, and that special calibrations would not be necessary for various market areas. It is further an object of the invention that the measuring device with the data transfer could be achieved by simple and reliable arrangements.

The above-described problems are eliminated and the above-defined objects are achieved by means of a device of the invention, which comprises: a sensor connected to said two support elements and providing an electrical output proportional to the spacing of said support elements and accordingly proportional to dimension of the patient's head therebetween; and a control unit or a connection feeding said electrical output transformed or non-transformed to the exposure control means, so adjusting the current and/or the voltage of the X-ray tube and/or the exposure time to be at one of a plurality of predetermined levels, each of which being in a predetermined relationship with the spacing of said support elements. The above-described problems are eliminated and the above-defined objects are achieved by means of a method of the invention, which prior to exposure comprises the steps: while resting the patient's head against support means in an X-ray apparatus, at least support elements of a support element pair of said support means, said support elements being connected to a sensor, are moved towards each other and against the substantially opposite sides of the patient's head; an electrical output from the sensor, representing the spacing of the support elements and accordingly the spacing between the opposite sides of a patient's head, is fed to adjust or display a current and/or a voltage of an X-ray tube and/or to adjust or display an exposure time of the radiation from the X-ray tube.

According to the invention the problems described are surprisingly solved by detecting one outer dimension, typically the width of the patient's head utilizing the adjustable head support elements inherent in every the X-ray panoramic and cephalometric apparatuses, transforming this mechanical dimension data by simple electrical unit or sensor into electrical data, which is proportional to the mechanical dimension, and transferring this electrical data in such configuration into the exposure control means of the apparatus that the tube current and/or tube voltage and/or the exposure time is altered or adjusted to a level, which is correct for image receptor. This device and method of the invention so creates exposure automatics, which is indeed very simple and requires a minimum of additional components as compared to standard panoramic and cephalometric apparatuses. The accuracy of this invented device and method is good enough in practice. The device and method of the invention further eliminates the effects of human inconsistencies concerning the operator, because it is an automatic system in question.

BRIEF DESCRIPTION OF THE DRAWINGS

The invention is now described in detail with reference made to the appended drawings.

DESCRIPTION OF THE PREFERRED EMBODIMENTS

Figure 1:
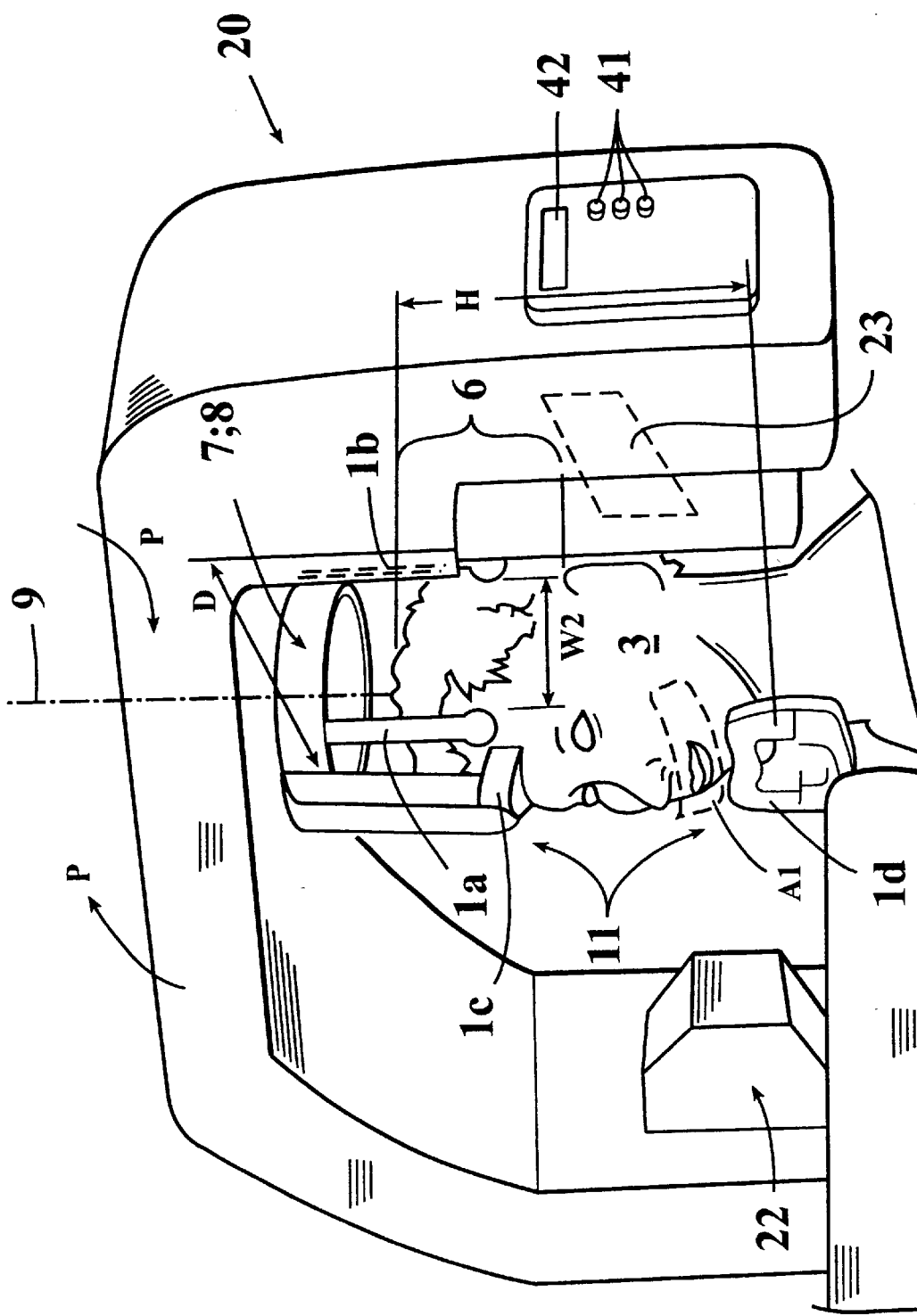
FIG. 1 illustrates generally a panoramic X-ray imaging apparatus, including a patient's head support system, parts of which are utilized for the exposure automatics according to one embodiment of the invention.
Figure 2:
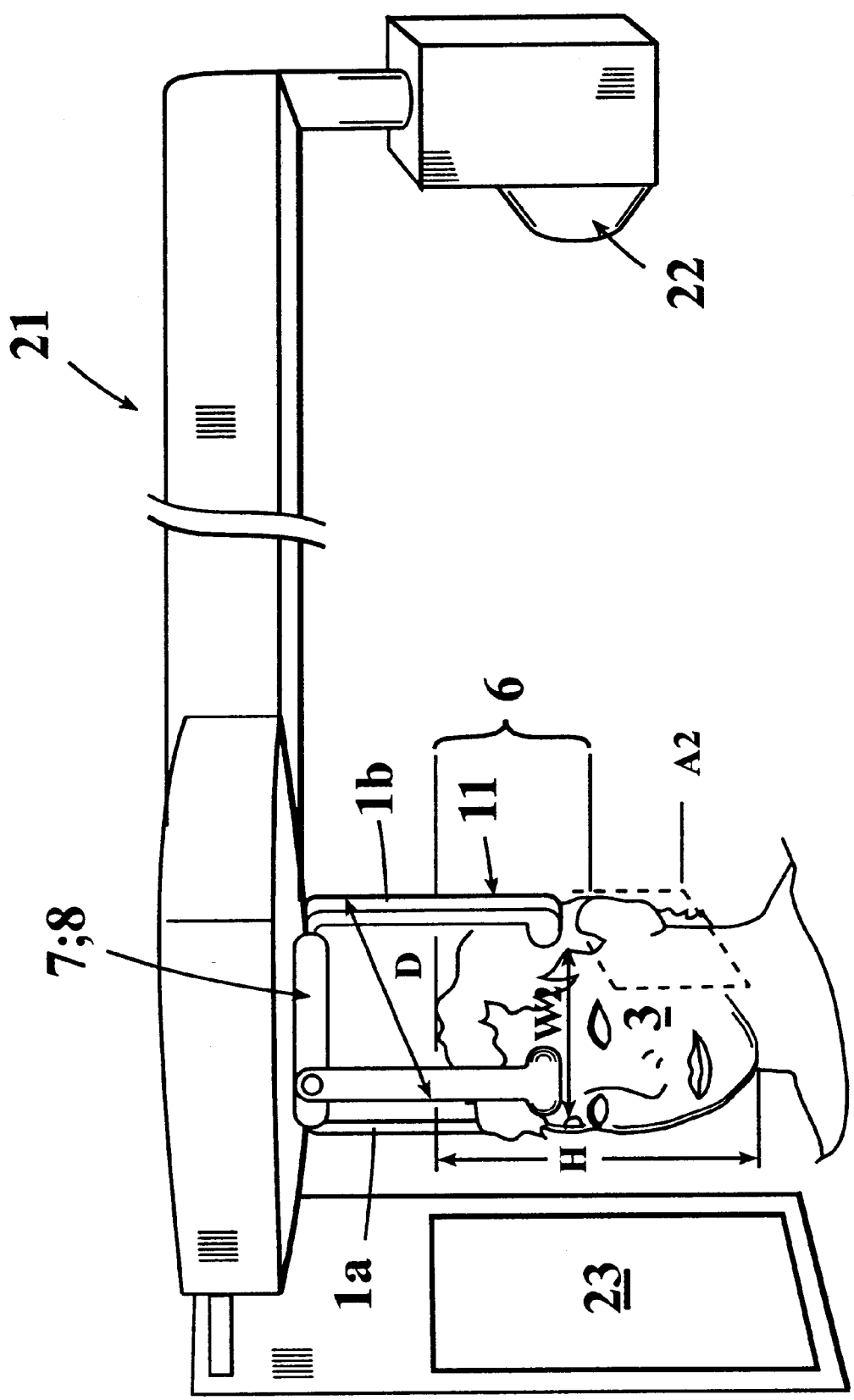
FIG. 2 illustrates generally a cephalometric X-ray imaging apparatus, including a patient's head support system, parts of which are utilized for the exposure automatics according to another embodiment of the invention.

In FIGS. 1 and 2 are shown an X-ray panoramic and cephalometric apparatus 20, and 21 respectively for imaging a part of a patient's head 3. Both the cephalometric and the panoramic apparatus comprises an X-ray tube 22 with an exposure control means 10, not visible in FIGS. 1 and 2, and adjustable support means 11 for a patient's head to immobilize the head 3 during exposure of the image. Panoramic apparatus is used for taking an X-ray image from the teeth of the patient altogether from one end of the jawbone to the other end of the jawbone, i.e. the jaw area A1 of the patient's head, whereupon a single continuous image from the curved target is formed. For this purpose both the X-ray tube 22 and an image receptor 23, e.g. a radiation sensitive sheet, are rotated P around the patient's head 3 during the exposure to have a pivot movement P. Panoramic imaging and its details are widely known, and accordingly the apparatus and the imaging method is not described more in detail. Cephalometric apparatus is used for taking an X-ray image from the head 3 or e.g. neck area A2, including e.g. the cervical spinea and the lower cranial section of the patient, whereupon a single planar image from the patient's head is formed. For this purpose both the X-ray tube 22 and the radiation sensitive image receptor 23 are kept stationary during the exposure. Cephalometric imaging and its details are widely known, and accordingly the apparatus and the imaging method is not described more in detail. The image receptor or a radiation sensitive sheet 23 can be an X-ray sensitive photographic film, or an X-ray sensitive image plate, or any other type of X-ray sensitive means, which could be used for reading the intensities of radiation penetrated the head parts of interest. For a proper exposure of the image receptor 23 the tube current, generally marked as It, and the tube voltage, generally marked as Ut, of the X-ray tube shall be in an appropriate level, and the exposure time, generally marked as T, shall have an appropriate duration. The exposure time T can be controlled by a shutter 39, though shutters are not generally used nowadays, prohibiting radiation R from reaching the target, i.e. the head, all but the period of exposure, or by a timer 38 switching the X-ray tube current/voltage at the beginning of the exposure from OFF-state to ON-state and at the end of exposure from ON-state to OFF-state in cephalometric apparatus, or by a rotational speed control unit 37 in panoramic apparatus, whereupon of course taking account of the slot widths of the blinds. These components are generally known, and are so not described more in detail.

The support means 11 are provided with at least two support elements 1a, 1b with a variable spacing W1 therebetween on the opposite sides of the patient's head. Typically the support means are provided with four support elements 1a–1d in the panoramic X-ray apparatus 20, and with three support elements 1a–1c in the cephalometric X-ray apparatus, and accordingly the two support elements 1a, 1b, utilized for the detection of the target dimensions according to the invention, are e.g. a part of a 4-point head support system in a panoramic apparatus 20, and e.g. a part of a 3-point head support system in a cephalometric apparatus 21. Of course it is possible to use a 2-point head support system in the panoramic apparatus 20 as well as in the cephalometric apparatus 21. These at least two support elements of the support means are movable towards each other and from each other, generally both horizontally and vertically in the panoramic apparatus 20, and generally horizontally in the cephalometric apparatus 21, for positioning against the patient's head, preferably against the cranial part of the head, which is substantially outside the image areas A1 and A2, prior to an exposure. In the panoramic apparatus 20 the patient shall press his/hers chin against the lower front support element 1d and his/hers forehead against the upper front support element 1c, whereafter the upper side support elements 1a and 1b are moved in a lateral direction M towards each other until in contact with the opposite sides of the head, generally in the temporal region or in the area of the widest point of the head 3 with a spacing W2 therebetween. In the cephalometric apparatus 21 the patient shall press his/hers forehead against the upper front support element 1c, whereafter the upper side support elements 1a and 1b are moved in a lateral direction M towards each other until in contact with the opposite sides of the head, e.g. in the temporal regions or in the area of the widest point of the head 3 with a spacing W2 therebetween. Most generally the two opposite support elements 1a, 1b in the cephalostatic apparatus are pushed in the ears of the patient in order to obtain a proper position of the patient's head and an immobilization thereof, but in this case the too, the spacing W2 between the opposite sides of the head is obtained. It can be understood that the height H of the head 3, between the chin and the parietal section, can be measured by support vertically moving elements not shown in the figures, as well as the depth D of the head 3, between the forehead and the occipital section, can be measured by laterally moving support elements not shown in the figures. It is however believed that the alternative of measuring the spacing between the temporal regions or between the points farthest from each other in the transversal direction of the head and in the cranial part of the head, shown in the figures, would have good interdependence or correlation with the bone thickness of the head, which bone thickness is the very property affecting exposure. This selected alternative has the advantage, that no additional support elements are needed, as compared to standard X-ray apparatuses.

Figure 3:
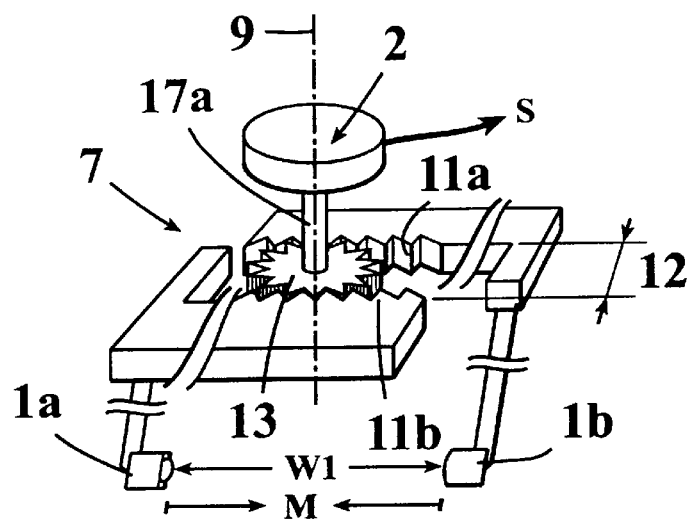
FIG. 3 and 4 illustrates two of the several alternatives for a conversion mechanism, which provides the movement of the support elements in the head support system to a sensor unit according to the invention, for obtaining a value proportional to the spacing between the opposite sides of a head.
Figure 4:
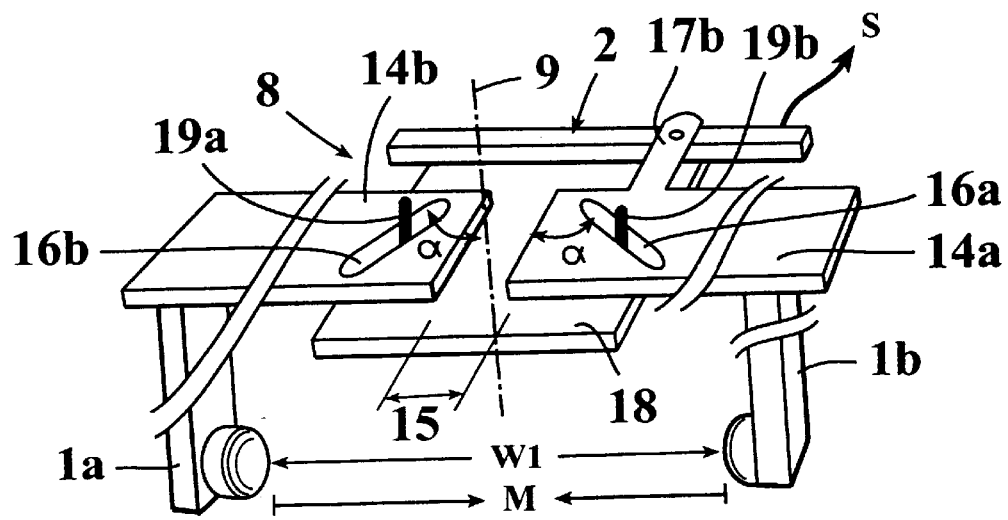

For determining the exposure values, i.e. the tube current It and/or the tube voltage Ut of the X-ray tube and/or the exposure time T of the image receptor, and for adjusting the exposure values into the exposure control means 10 the panoramic/cephalometric apparatus according to the invention is provided with a device comprising a sensor 2 connected to two opposite support elements, preferably to the support elements 1a and 1b. The sensor 2 or optionally sensors provide(s) an electrical output S proportional to the spacing W1 of said support elements 1a, 1b and accordingly proportional to dimension W2 of the patient's head therebetween. For this purpose the support elements 1a, 1b are preferably movable in a lateral direction M, which is e.g. substantially perpendicular to a length of the patient and against the cranial part 6, which means also the area of the patient's ears, of the patient's head to detect the width W2 or the depth D thereof. As described above the detection of the width W2 of the head 3 is preferred. If the alternative, in which the height H is detected, is used the support elements shall be moved vertically. The movement M of the support elements are transformed into a form, which can be read into an electrical signal, via a conversion mechanism 7 or 8 connected to the sensor 2 and the two support elements 1a, 1b so that each spacing W1 of the support elements has a respective electrical value S. As can be understood each spacing W1 of the two support elements are identical or—when possible errors are included—practically identical with the spacing W2 between the opposite sides of the head. The conversion mechanisms 7 and 8 connects the opposite support elements 1a and 1b with each other so that they move symmetrically in respect to the center line 9 or center plane therebetween, which is an important feature in case a rotary sensor is used, and especially in case of panoramic imaging, where this center line 9 is also the pivot/rotation P axle of the apparatus, as shown in FIG. 1. This symmetry of movements can be reached e.g. with two pinion racks 11a and 11b, which are extending along each other from the support elements in the movement direction M of the support elements 1a, 1b, positioned towards each other with a distance 12 therebetween, and with a cogged wheel 13 between the pinion racks 11a, 11b in engaging contact therewith, or alternatively with two first plates 14a and 14b, which are extensions of the support elements in the movement direction M of the support elements 1a, 1b with a distance 15 therebetween and each provided with a guide slot 16a, 16b having identical slope angles a in respect to a plane perpendicular to said moving direction M, and a second plate 18 with integrated guide pins 19a, 19b each in a respective guide slot 16a, 16b, which second plate 18 is movable in a direction perpendicular to the movement direction M of the support elements only. It can be constructed other kinds of conversion mechanisms, too. The movable part of the sensor 2 is attached to some appropriate part of the conversion mechanisms 7 and 8, in case of a rotary type sensor the sensor axle 17a is fixed preferably to the cogged wheel 13 as in FIG. 3, and in case of a linear type sensor the sensor slide 17b is fixed to one of the first plates 14a, 14b, as in FIG. 4, or to the second plate.

Figure 5:
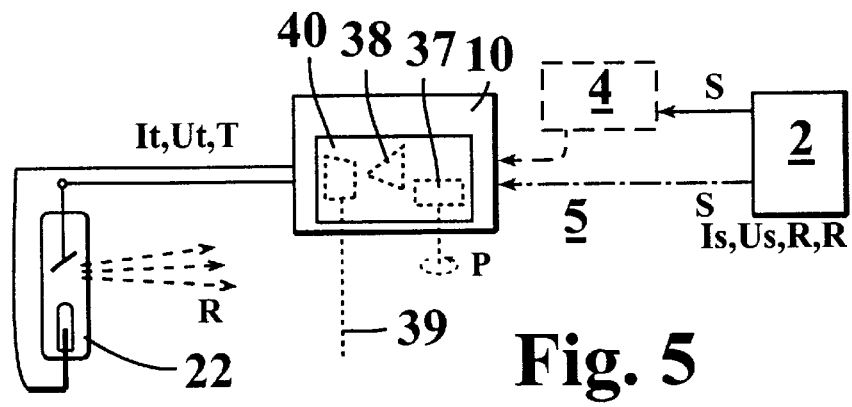
FIG. 5 illustrates the principles for transferring the dimensional data of the patient as obtained from the sensor unit to the exposure control means for adjustment of the exposure values effected by the X-ray tube and/or the exposure values effected by a shutter, timer or a rotational speed, with alternatives marked with dashed lines.
Figure 6A:
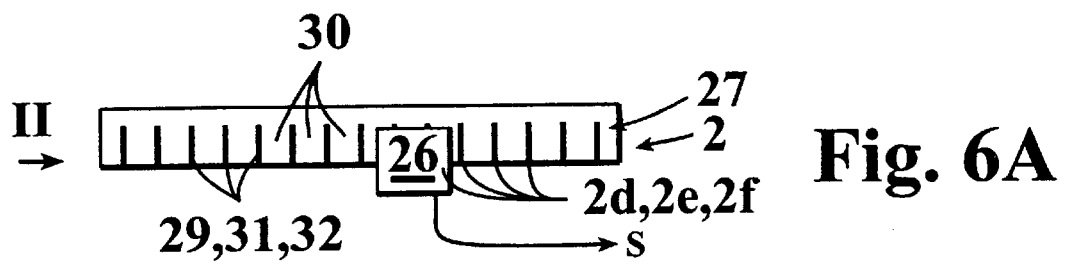
FIG. 6A to 6D illustrates schematically various sensor constructions—optical sensor, capacitive sensor, resp. electrical pulse counting detector—for detection of the position of the support elements of the head support system, in a direction I perpendicular to the movement of a slide as shown in FIGS. 6B to 6D, and in a direction II parallel with the movement of a slide as shown in FIG. 6A respectively. The sensor part shown can be a section of a linear type sensor of FIG. 4, or of a rotary type sensor of FIG. 3.
Figures 6B, 6C, 6D:
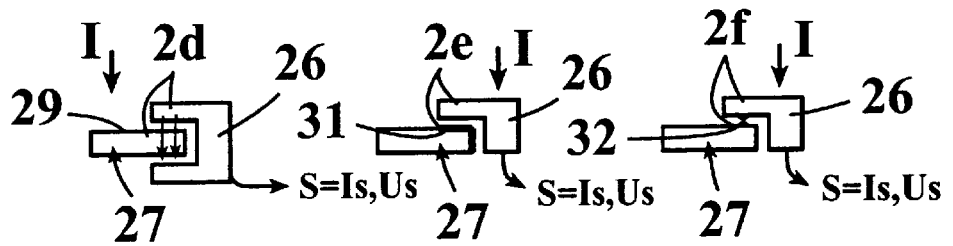
Figure 7A:
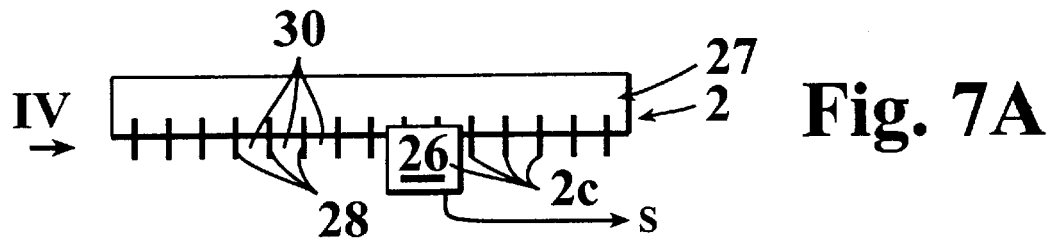
FIG. 7A and 7B illustrates schematically a sensor constructions—magnetic sensor—for detection of the position of the support elements of the head support system, in a direction III perpendicular to the movement of a slide as shown in FIG. 7B, and in a direction IV parallel with the movement of a slide as shown in FIG. 7A. The sensor part shown can be a section of a linear type sensor of FIG. 4, or of a rotary type sensor of FIG. 3.
Figure 7B:
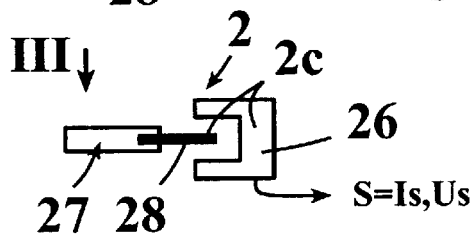
Figure 8A:
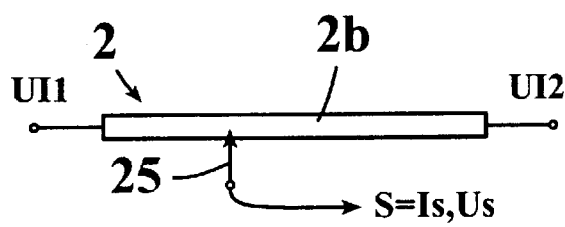
FIG. 8A to 8C illustrates schematically three sensor constructions—variable resistance sensor, a potentiometer sensor and a variable inductance sensor—for detection of the position of the support elements of the head support system, in a direction perpendicular to the movement of a slide, in same view as in FIGS. 6A, 7A. The sensor part shown can be a section of a linear type sensor of FIG. 4, or of a rotary type sensor of FIG. 3.
Figure 8B:
Figure 8C:
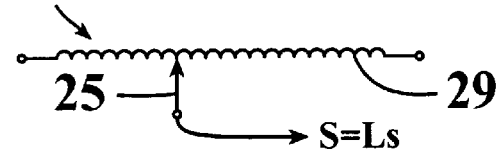

The sensor 2, the slide 17b or axle 17a of which is attached to the conversion mechanism can be a variable resistance 2a, whereupon the electrical output S of the sensor is connected to a voltage/current source U&I via a resistance part having its value dependent on the position of a contact element 25, or a potentiometer 2b, whereupon the electrical output S of the sensor is taken via a contact element 25 from between the two in counter directions variable resistance parts the ends of which are connected to different voltages $UI_1$ and $UI_2$. Analogous with the above described principles, a sensor 2 based on a variable inductance 2g or a variable voltage, like a variable transformer, can be designed, with a contact element 25 moving along a winding of a conductor around a core. Variable voltage from a sensor slide of a variable transformer is self explanatory, but using the variable inductance thereof requires an oscillator and a frequency detecting instrument as well as an frequency-output signal (=electrical output S) converter, like an A/D-converter or an A/A-converter. The sensor 2 can also be a magnetic position detector 2c comprising a sensor slide 26, which includes a magnetic detector, e.g. a so called Hall-element and a counter unit. A marker part 27 of the position detector consists of a plurality of ferromagnetic pieces 28 in intervals 30, whereupon the counter counts the number of ferromagnetic pieces from one end of the marker part and so the position of the sensor slide 26. The sensor 2 being an optical position detector 2d, it comprises a sensor slide 26, which includes a radiation source emitting electromagnetic radiation with a wavelength or a wavelength band, e.g. light and a radiation sensitive detector, e.g. a light detector, and a counter unit. The sensor also comprises a marker part 27 consisting of a plurality of measuring radiation, e.g. light, reflective or non-reflective or transmitting or non-transmitting pieces or surface sections 29 in intervals, the intervals 30 having a contrary property, i.e. they are a non-reflective or reflective or non-transmitting or transmitting material, whereupon the counter counts the number of said pieces or surface sections 29 from one end of the marker part and so the position of the sensor slide 26. When the reflective properties are utilized the radiation source and the radiation detector are positioned on one side of the marker part 27, whereas in case of utilizing transmission properties the radiation source and the radiation detector are positioned on the opposite side of the marker part 27 directed towards each other. In case of a capacitive position detector 2e, it comprises a sensor slide 26, which includes a capacitor plate and a capacitance sensitive trigger circuit and a counter unit. A marker part 27 of the position detector consists of a plurality of opposed capacitor plates 31 in intervals, the capacitor plates connected to a voltage source, whereupon the counter counts the number of the capacitor plates 31 from one end of the marker part and so the position of the sensor slide 26. Further if the sensor is a position detector 2f operating with electrical pulse counting, it comprises a sensor slide 26, which includes an electrical contact, a voltage sensitive trigger circuit and a counter unit. A marker part 27 of the position detector consists of a plurality of opposed electrical contacts 32 in intervals, the electrical contacts connected to a voltage source, whereupon the counter counts the number of the electrical contacts 32 from one end of the marker part and so the position of the sensor slide 26. As can be readily understood the position of the sensor slide 26 is proportional to the position, that is spacing W1, of the support elements 1a and 1b, and accordingly an electrical output S proportional to said spacing is received. These various position detectors are examples and any position detector of a different type can be used instead. It shall be understood that any of the sensors in FIGS. 6A to 8C can be part of a linear type sensor 2 of FIG. 4, or part of a rotational type sensor of FIG. 5, the only difference being that the marker part 27 is either a linear component or a circular component. The details of the position detectors as disclosed above are known as such, and are not described more in detail.

Depending on type of the position detector 2a, 2b, 2c, 2d, 2e, 2f, 2g different type of electrical output S is formed, whereupon it can be an electrical resistance value Rs, an inductance value Ls, a voltage value Us or a current value Is or a numerical value Ns or a combination of these. Any sensor 2 can be arranged to give an electrical output S in numerical form, like binary data, or in analog form, depending on the general design of exposure control means 10. If conversion of the electrical output from the sensor is needed, this can be done using electronic circuitry known as such.

Figure 9:
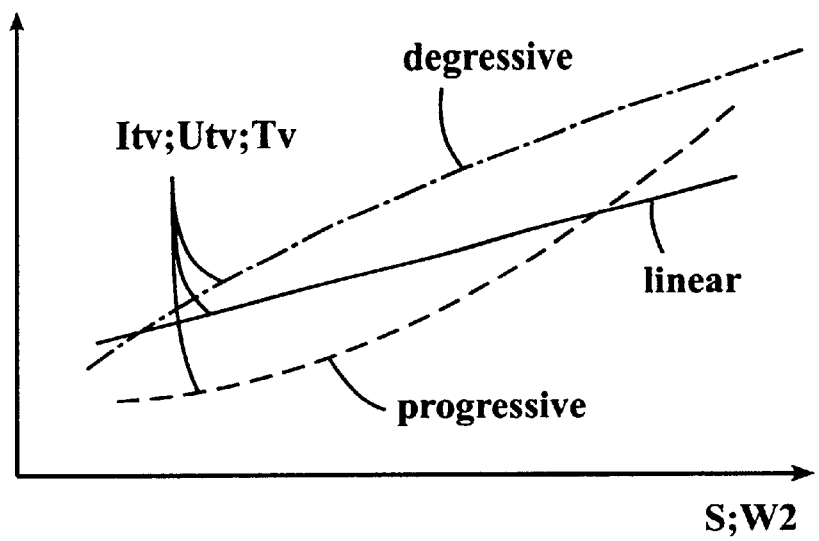
FIG. 9 illustrates the continuously—either linear or progressive or degressive—variable dependence of the exposure values, that is the tube current and/or the tube voltage and/or the exposure time, as compared to the sensor output proportional to the dimension of a patient's head.
Figure 10:
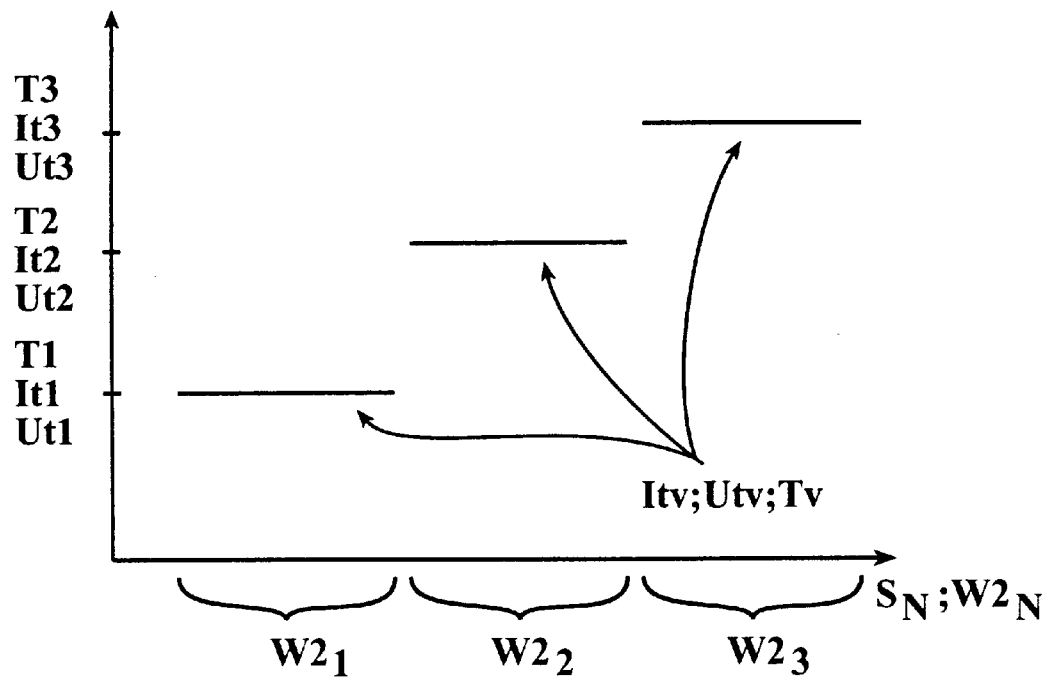
FIG. 10 illustrates the variably discontinuously—several exposure values, different from each other and constant over specified ranges of dimensions—variable dependence of the exposure values, that is the tube current and/or the tube voltage and/or the exposure time, as compared to the sensor output proportional to the dimension of a patient's head.

The device according to the invention further comprises a control unit 4 or a connection 5 feeding said electrical output S in a transformed or in a non-transformed form to the exposure control means 10, so adjusting the tube current It and/or the tube voltage Ut of the X-ray tube and/or the exposure time T of the image receptor, i.e. the duration of radiation R into the image receptor, through a timing unit 40. The timing unit 40 means any components used for varying or controlling exposure time, and especially a shutter 39 an/or a timer 38, or a rotational speed control unit 37. In case the signal or electrical output S from the sensor control unit 4 is in numerical form, an electronic programmed processor is utilized, which switches the exposure control means 10 to provide the X-ray tube a preset current It level, and/or a preset voltage Ut level, and/or a preset exposure time T level respective to each value of the electrical output S of the sensor. The electronic programmed processor can be programmed, in any of the known ways, to deliver a preset current It level and/or a preset voltage Ut level to the X-ray tube and/or a preset exposure time T of the radiation R via the exposure control means 10. The tube current It and/or tube voltage Ut and/or an exposure time T can be programmed to be proportionally, i.e. linearly, or non-linearly, i.e. progressively or degressively dependent on the spacing W1 between the support elements 1a, 1b, as shown in FIG. 9, or alternatively stepwise dependent on the spacing W1 between the support elements 1a, 1b, as shown in FIG. 10. In case the signal or electrical output S from the sensor control unit 4 is in analog form, the connection 5 can be a direct or an indirect electrical connection between the sensor 2 and the exposure control means 10, which connection delivers a preset current It level and/or a preset voltage Ut level to the X-ray tube, and/or a preset exposure time T of the radiation trough the exposure control means 10. For this purpose the electrical output S of the sensor have preselected values, i.e. the above disclosed electrical resistance value, or inductance value, or voltage value, which are proper in generating said current It level and/or voltage Ut level and/or said exposure time T in the exposure control means 10. The analog electrical output S can be proportionally, i.e. linearly, or non-linearly, i.e. progressively or degressively dependent on the spacing W1 between the support elements 1a, 1b, as shown in FIG. 9, or alternatively stepwise dependent on the spacing W1 between the support elements 1a, 1b, as shown in FIG. 10. All these analog electrical outputs S, whereupon also the stepwise dependency shall be considered as analog signal, because no real numerals are used, can be obtained directly from the sensor 2, which has the inductance or resistance or voltage or current carrying component respectively configured to change its value along its length, which corresponds the linear or rotary movement of the sensor slide 26, linearly or non-linearly or stepwise within the required range(s). Hereby the tube current It and/or the tube voltage Ut and/or the exposure time T is/are set at one of a plurality of predetermined levels, each of which being in a predetermined relationship with the spacing W1 of said support elements. It shall be kept in mind that if only one or two of three values effecting exposure, that is tube current It, the tube voltage Ut, the exposure time T, is selected according to the invention, the other two or one of the values is kept constant. There is so always a tube current and a tube voltage and an exposure time in a single image taking operation, but according to the invention any of these, or any two of these, or all three can be selected after measuring the dimension W2 of the patient's head.

Above is an totally automatic system described, in which the exposure values It and/or Ut and/or T selected are directly the final exposure values. The most simple way to this automatics is to arrange the sensor 2 be one component of the exposure control means 10, but computerized automatics or automatics with other kind of electronics are also applicable. Another option is a semi-automatic system if required, whereupon the panoramic or cephalostatic apparatus is provided with a display 42 and external control elements 41 like knobs or press buttons, which are connected to the exposure control means 10 or are external parts of the sensors 2, e.g. extensions of the sensor slide 26 or contact element 26, and through which the operator of the apparatus is able to read and change one or more of the three exposure values, at first selected and suggested automatically by the exposure control means 10 on the basis of the spacing W1. The unaltered or altered exposure values are then set by the operator by e.g. pressing an appropriate button or the like among the external control elements 41.

So shortly defined, the current It level and/or the voltage Ut level provided to the X-ray tube 22 and/or the exposure time T level provided to the timing unit 40 by said preselected electrical output S of the sensor and the connection 5, or by the electronic programmed processor 4 is either a continuously variable value $It_V$ and/or $Ut_V$ and/or $T_V$ dependent on the electrical output S from the sensor, or alternatively a substantially constant value $It_N$ and/or $Ut_N$ and/or $T_N$ over predefined ranges $S_N$ of the electrical outputs and accordingly constant within ranges $W2_N$ of dimensions W2 of the patient's head 3 therebetween. This latter alternative is described more in detail. In principle it means, that there are at least two $W2_1$, $W2_2$ or at least three predefined ranges $W2_1$, $W2_2$, $W2_3$ of dimensions of the patient's head, each of which ranges corresponds one substantially constant exposure value, i.e. the exposure control means 10 delivers at least two or at least three levels of exposure values respectively to the X-ray tube 22 and to the timing unit 40. These levels of the constant exposure values so are a first tube current $It_1$ and/or a first tube voltage $Ut_1$ and/or a first exposure time $T_1$, and further at least a second tube current $It_2$ and/or a second tube voltage $Ut_2$ and/or a second exposure time $T_2$, and optionally a third tube current $It_3$ and/or a third tube voltage $Ut_3$ and/or a third exposure time $T_3$ of the X-ray tube 22 and the timing unit 40 respectively, as shown in FIG. 10, leading to a set of exposure values changing/varying stepwise. It is believed that three or possibly four levels of the exposure values, each of which corresponds to one range $W2_1$, $W2_2$, $W2_3$ etc. of the dimension of the patient's head and so corresponding a range of spacings W1 between the support elements 1a, 1b, are a proper amount of levels for practice. The electrical, electronic and mechanical construction of the timing unit can be of any conventional or new type familiar to an expert at the field of technology, as is the X-ray tube 22 with its control circuits, and so it is not described here.

As already described the method according to the invention for determining exposure values for an X-ray panoramic and/or cephalometric imaging of a patient's head 3 comprises the following steps. Prior to exposure and while resting the patient's head 3 against support means 11 in an X-ray apparatus 20; 21, at least the support elements 1a, 1b of a support element pair of said support means are moved M towards each other and against the substantially opposite sides of the patient's head. This moving M of the support elements 1a, 1b as a pair, because these two elements are connected to each other as earlier described, can be performed manually by an operator of the X-ray apparatus, or automatically upon starting the procedure. Generally said, the support elements 1a, 1b of the support means 11 are preferably moved M against such parts 6 of the patient's head, which are not included in the imaging area A1 or A2 of the head 3. An electrical output S from the sensor 2, to which the support elements 1a and 1b are connected, accordingly representing the spacing W1 of the support elements and so corresponding to the spacing W2 between the opposite sides of a patient's head 3, is automatically delivered to the exposure control means 10 to select a current It and/or a voltage Ut for the X-ray tube 22 and/or an exposure time T for the timing unit 40. Thereafter the exposure values selected, being a current It, and/or a voltage Ut of the X-ray tube 22 and/or an exposure time T of the timing unit 40, is set either manually, upon activation by the operator, or automatically to the X-ray panoramic and/or cephalometric apparatus 20; 21. The exposure control means 10 can display the selected exposure values for the evaluation by the operator, especially in case of utilizing said manual step, whereupon the operator can alter the exposure values or some of them, if deemed necessary. For this semi-automatics the panoramic or cephalometric apparatus are provided with a display unit 42 and external control knob(s) or the like 41, through which the operator can make the alteration of one or several of the exposure values, followed by manual setting/feeding of the values into the exposure control means 10.

The exposure values, being a current It and/or a voltage Ut of the X-ray tube 22, and/or an exposure time T of the timing unit 40, are automatically selected from a group of exposure values having at least two preset levels of said current $It_1$, $It_2$, $It_3$; $It_V$ or said voltage $Ut_1$, $Ut_2$, $Ut_3$; $Ut_V$ or said exposure times $T_1$, $T_2$, $T_3$; $T_V$, whereupon each of said levels corresponds a predefined range of bone thickness in the patient's head 3. According to the invention it is also possible to use different combinations of the types of selectable exposure values. So one or two of the three exposure values—tube voltage and/or tube current and/or exposure time—can be continuously variable according to dimension W2, as shown in FIG. 9, and two or respectively one of the three exposure values—tube voltage and/or tube current and/or exposure time—can be substantially constant over the predefined ranges with values changing or varying stepwise according to dimension W2, as shown in FIG. 10. If two of the exposure values are continuously variable, and also in case when all three of the exposure values are continuously variable, said two or three exposure values can have any of the three different forms, i.e. follow the linear and/or the degressive and/or the progressive curve of FIG. 9. Further it is possible to utilize a combination of exposure values, in which all of the three exposure values are of the same type, that is either continuously variable or varying stepwise. In this context it is emphasized that above said preset levels means both the limited amount of exposure levels, as illustrated in FIG. 10, and the unlimited amount of exposure levels, as illustrated in FIG. 9. As can be seen the method can be configured to be totally automatic or be semi-automatic of different types.

What is claimed is:

1. A device for determining exposure values in an X-ray panoramic and/or cephalometric apparatus (20, resp. 21) for imaging patient's head (3) or a part thereof, which apparatus comprises an X-ray tube (22), an exposure control means (10) providing a tube voltage, a tube current and an exposure time, and adjustable support means (11) for a patient's head, said support means being provided with at least two support elements (1a, 1b) with a variable spacing (W1) therebetween on the opposite sides of the patient's head, and said support means being adapted for positioning against the patient's head prior to an exposure, characterized in that said device comprises:
   a sensor (2) connected to said two support elements and providing an electrical output proportional to the spacing (W1) of said support elements (1a, 1b) and accordingly proportional to dimension (W2) of the patient's head therebetween; and
   a control unit (4) or a connection (5) feeding said electrical output (S) transformed or non-transformed to the exposure control means (10), so adjusting the current (It) and/or the voltage (Ut) of the X-ray tube and/or the exposure time (T) to be at one of a plurality of predetermined levels, each of which being in a predetermined relationship with the spacing (W1) of said support elements.

2. A device according to claim 1, characterized in that said sensor (2) is a variable resistance (2a), or a potentiometer (2b), or a magnetic position detector (2c), or an optical position detector (2d), or a capacitive position detector (2e), or a position detector (2f) operating with electrical pulse counting.

3. A device according to claim 1, characterized in that said control unit (4) is an electronic programmed processor, which switches the exposure control means (10) to provide a preset exposure time (T) to a timing unit (40) of the apparatus, and/or a preset current (It) level, and/or a preset voltage (Ut) level to the X-ray tube, respective to each value of the electrical output (S) of the sensor; and in that the electrical output (S) of the sensor (2) is a numerical value (Ns).

4. A device according to claim 1, characterized in that said connection (5) is an electrical connection between the sensor (2) and the exposure control means (10) for providing a preset exposure time (T) to a timing unit (40) of the apparatus, and/or a preset current (It) level, and/or a preset voltage (Ut) level to the X-ray tube; and that the electrical output (S) of the sensor have preselected values, which are proper in generating said exposure time (T) or current (It) level or voltage (Ut) level in said exposure control means (10).

5. A device according to claim 4, characterized in that the electrical output (S) of the sensor (2) is an electrical resistance (Rs) and/or as electrical voltage (Us) and/or an electrical current (Is) and/or an electrical inductance (Ls).

6. A device according to claim 3 or 4, characterized in that the current (It) levels or the voltage (Ut) levels provided to the X-ray tube (22), or the exposure times (T) provided to the timing unit (40) by said preselected electrical output (S) of the sensor and the connection (5), or by the electronic programmed processor (4) are:

- a continuously variable value ($It_V$ and/or $Ut_V$ and/or $T_V$) proportional to the electrical output (S) from the sensor; or
- substantially constant value ($It_N$ and/or $Ut_N$ and/or $T_N$) over predefined ranges ($S_N$) of the electrical outputs and accordingly constant within ranges ($W2_N$) of dimensions (W2) of the patient's head (3) therebetween.

7. A device according to claim 6, characterized in that there are at least two ($W2_1$, $W2_2$) or at least three predefined ranges ($W2^1$, $W2_2$, $W2_3$) of dimensions of the patient's head, so as to provide at least two or at least three-levels of exposure respective said constant values ($T_1$ and/or $It_1$ and/or $Ut_1$; $T_2$ and/or $It_2$ and/or $Ut_2$; resp. $T_3$ and/or $It_3$ and/or $Ut_3$) in the timing unit (40) and in the X-ray tube (22).

8. A device according to claim 1, characterized in that said support elements (1a, 1b) are lateral supports adapted for movement (M) in a direction substantially perpendicular to a length of the patient (3) and against the cranial part (6) of the patient's head to detect the width thereof.

9. A device according to claim 8, characterized in that said timing unit (40) is a shutter (39) and/or a timer (38) for the radiation from the X-ray tube, in cephalometric apparatuses, or a rotational speed control (37) for the pivot movement (P) of the panoramic apparatuses.

10. A device according to claim 1, characterized in that the apparatus (20, 21) further comprises a display (42) and external control means (41) for manual altering of one or more of the exposure values (It, Ut, T) adjusted by the exposure control means (10).

11. A method for determining exposure values for an X-ray panoramic and/or cephalometric imaging of a patient's head (3), in which method: an individual spacing (W2) between the opposite sides of the patient's head is detected; exposure values (It and/or Ut and/or T) are defined dependent on said detected spacing; and said exposure values are used for the imaging of the patient's head or a section thereof, characterized in that said method prior to exposure further comprises the steps:

while resting the patient's head (3) against support means (11) in an X-ray apparatus (20; 21), at least support elements (1a, 1b) of a support element pair of said support means, said support elements being connected to a sensor (2), are moved (M) towards each other and against the substantially opposite sides of the patient's head;

an electrical output (S) from the sensor, representing the spacing (W1) of the support elements and accordingly the spacing (W2) between the opposite sides of a patient's head (3), is fed to adjust or display a current (It) and/or a voltage (Ut) of an X-ray tube (22) and/or to adjust or display an exposure time (T) of the radiation (R) from the X-ray tube.

12. A method according to claim 11, characterized in that the support elements (1a, 1b) of the support element pair are moved (M) against such parts (6) of the patient's head, which are not included in the imaging area (A1 or A2) of the head (3).

13. A method according to claim 11, characterized in that the exposure values, being a current (It), and/or a voltage (Ut) of the X-ray tube and/or the exposure time (T) into the image receptor (23), are selected from a group of exposure values having at least two preset levels of said current ($It_1$, $It_2$; $It_V$), and/or said voltage ($Ut_1$, $Ut_2$; $Ut_V$), and/or at least two preset levels of the exposure time ($T_1$, $T_2$) whereupon each of said levels corresponds a predefined range of bone thickness in the patient's head (3).

14. A method according to any one of claims 11 to 13, characterized in that the exposure values, being a current (It) and/or a voltage (Ut) of the X-ray tube and/or the exposure time (T) for the image receptor (36), is set either by manual selection of altered or non-altered exposure values displayed, or by automatical adjustment to the X-ray panoramic and/or cephalometric apparatus (20; 21).

* * * * *